United States Patent [19]

Blaser

[11] Patent Number: 5,434,306
[45] Date of Patent: Jul. 18, 1995

[54] PROCESS FOR THE PREPARATION OF O-SUBSTITUTED OXIMES

[75] Inventor: Denis Blaser, Monthey, Switzerland

[73] Assignee: Ciba-Geigy Corporation, Ardsley, N.Y.

[21] Appl. No.: 333,910

[22] Filed: Nov. 3, 1994

[30] Foreign Application Priority Data

Nov. 25, 1993 [CH] Switzerland .................. 3525/93

[51] Int. Cl.$^6$ ............................................ C07C 249/04
[52] U.S. Cl. ...................................... 564/256; 564/257
[58] Field of Search ................................. 564/256, 257

[56] References Cited

U.S. PATENT DOCUMENTS 4,545,807 10/1985 Fráter et al. .............................. 71/92
4,687,849 8/1987 Fráter et al. .......................... 544/354

OTHER PUBLICATIONS

Mong et al. "Synthesis of Polyurethanes Derived from Oximes and Their Photodegradation", *Journal of Polymer Science* Polymer Chemistry Ed., vol. 10, 3405–3419 (1972).

R. Klavser et al., ACS Symposium Ser., 1991, Synth. Chem. Agrochem. 2, 443, pp. 226–235.

*Primary Examiner*—Peter O'Sullivan
*Attorney, Agent, or Firm*—Marla Mathias

[57] ABSTRACT

The invention relates to a process for the hydroxyalkylation of aldoximes and ketoximes by reacting said oximes with unsubstituted or substituted ethylene or propylene carbonate in the presence of a catalyst, which comprises the use of catalytic amounts of a N-alkylated, stable, organic amidinc base or a pyridine which is substituted by a secondary amino group. The compounds are important intermediates for the synthesis of herbicides.

21 Claims, No Drawings

PROCESS FOR THE PREPARATION OF O-SUBSTITUTED OXIMES

The present invention relates to a process for the preparation of O-ω-hydroxyalkyloximes by reacting oximes with alkylene carbonates in the presence of catalytic amounts of an amidine or a pyridine base.

These oximes are important intermediates for herbicides, inter alia those disclosed in U.S. Pat. Nos. 4,545,807 and 4,687,849.

U.S. Pat. No. 4,687,849 relates to a process for the preparation of 2-[(isopropylideneamino)oxy]ethanol, which comprises reacting acetone oxime in aqueous medium, in the presence of catalytic mounts of Ca-(OH)$_2$, with ethylene oxide. One drawback of this process is that ethylene oxide is difficult to produce on an industrial scale and can only be handled with stringent safety regulations, as it is highly explosive and extremely poisonous. Another drawback is that the process results in substantial amounts of wastewater that have to be purified. It is also already known that 2-[(isopropylideneamino)oxy]ethanol can be prepared by reacting acetone oxime with ethylene carbonate. Potassium fluoride and tetramethylammonium bromide can be used as catalysts for this reaction. This process is described, inter alia, in R. Klauser et al. in ACS Symposium Ser. 1991, 443, (Synth. Chem. Agrochem. 2), 226–235. The reaction without the use of catalysts and solvents has been described by S. I. Hong et al. in J. Polym. Sci. Part A-1, 1972, 10, 3405-19. Even at very high temperatures, yields of only 33% are obtained. These processes have serious ecological and economic disadvantages, for example that a heterogeneous reaction mixture is obtained and lengthy reaction times of up to 10 hours are required. The use of a fluoride complicates the working up of the reaction mixture on an industrial scale. A filtration and a washing step must be carded out subsequently. In addition, the wash-water has to be reprocessed.

It has now been found that, in homogeneous reaction media and in substantially shortened reaction times, it is possible to obtain at least equally high yields by using an organic amidine base or a pyridine base as catalyst. The desired product can be isolated in simple manner by distillation, while solvent and catalyst can likewise be recovered and reused. This ecological and economic process is therefore especially suitable for production on an industrial scale.

In one of its aspects, the invention relates to a process for the hydroxyalkylation of aldoximes and ketoximes by reacting said oximes with unsubstituted or C$_1$–C$_8$alkyl-substituted ethylene or propylene carbonate in the presence of a catalyst, which comprises the use of catalytic amounts of a N-alkylated, stable, organic amidine base or a pyfidine which is substituted by a secondary amino group.

Stable means that the amidine or pyridine base is substantially not decomposed under the chosen reaction conditions such as temperature and solvent.

N-Alkylated means that the N atom of the amino group of the amidine base or pyridine base is mono- or disubstituted by C$_1$–C$_8$alkyl, preferably by C$_1$–C$_4$alkyl, or the N atom is part of a ring of a mono- to tricyclic ring system.

It is preferred to use the process for the preparation of compounds of formula I

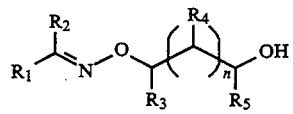

wherein R$_1$ and R$_2$ are each independently of the other hydrogen, C$_1$–C$_8$alkyl, C$_3$–C$_8$cycloalkyl, C$_1$–C$_8$haloalkyl, unsubstituted or C$_1$–C$_8$alkyl- or halogen-substituted phenyl, benzyl or phenylethyl, or R$_1$ and R$_2$, taken together, are unsubstituted or C$_1$–C$_8$alkyl- or halogen-substituted C$_2$–C$_7$alkylene, R$_3$, R$_4$ and R$_5$ are each independently of one another hydrogen or C$_1$–C$_8$alkyl, and n is 0 or 1, by reacting compounds of formula II

with compounds of formula III

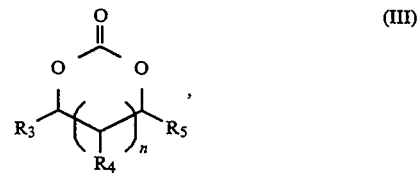

wherein R$_3$, R$_4$, R$_5$ and n have the meanings given above. In the compounds of formula I, n is preferably 0.

R$_1$ and R$_2$ as cycloalkyl preferably contain 5 or 6 carbon atoms. Typical examples of cycloalkyl are cyclopropyl, dimethylcyclopropyl, cyclobutyl, cyclopentyl, methylcyclopentyl, cyclohexyl and cycloheptyl.

Halogen within the scope of this invention will be taken to mean fiuoro, chloro, bromo or iodo. Fluoro, chloro or bromo are preferred, and fluoro or chloro are particularly preferred.

Haloalkyl which preferably contains 1 to 4 carbon atoms is typically: fluoromethyl, difluoromethyl, trifluoromethyl, chloromethyl, dichloromethyl, trichloromethyl, 2,2,2-trifluoroethyl, 2-fluoroethyl, 2-chloroethyl, 2,2,2-trichloroethyl, 1,1,2,2-tetrafluoroethyl as well as partially or completely chlorinated or fluorinated isopropyl, n-propyl, n-butyl, isobutyl, sec-butyl, tert-butyl, pentyl, hexyl, heptyl and octyl.

R$_3$, R$_4$ and R$_5$ are preferably hydrogen or C$_1$–C$_4$alkyl. Alkyl is typically methyl, ethyl, n- or isopropyl, n-, iso-, or tert-butyl. R$_3$, R$_4$, and R$_5$ are most preferably hydrogen.

In a preferred embodiment of the process, R$_1$ and R$_2$ are each independently of the other hydrogen or C$_1$–C$_8$alkyl, or R$_1$ and R$_2$ together form unsubstituted C$_2$–C$_7$alkylene, R$_3$ and R$_5$ are hydrogen or C$_1$–C$_4$alkyl, and n is 0.

A particularly preferred embodiment of the process is that wherein R$_1$ and R$_2$ are methyl, ethyl or propyl, R$_3$ and R$_4$ are hydrogen, and n is 0.

The amidine base contains the structural element —C—N=C—N—C—, which may be either open-chain compounds, an alicyclic ring or a bicyclic and tricyclic ring system that contains 4 to 8, preferably 5 or 6 ring members. The amidinc base preferably contains 4 to 20, more particularly 4 to 14 and, most preferably, 4 to 10, carbon atoms. The secondary amino group as substituent of pyridine preferably contains 2 to 24, more particularly 2 to 18 and, most preferably, 2 to 12, carbon atoms.

The organic amidine base preferably has the formula IV and the pyridine substituted by a secondary amino group preferably has the formula V

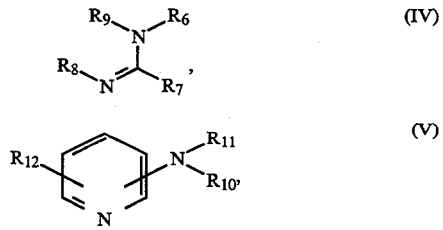

wherein $R_6$, $R_7$, $R_8$ and $R_9$ are each independently of one another $C_1$–$C_8$alkyl or $C_3$–$C_8$cycloalkyl, or $R_6$ and $R_7$, taken together, form a hydrocarbon radical containing 3 to 6 carbon atoms, and $R_8$ and $R_9$ have the meanings previously given, or $R_8$ and $R_9$, taken together, form a hydrocarbon radical containing 2 to 6 carbon atoms, and $R_6$ and $R_7$ are $C_1$–$C_8$alkyl or $C_3$–$C_8$cycloalkyl, or $R_6$ and $R_7$, taken together, form a hydrocarbon radical containing 3 to 6 carbon atoms, and $R_8$ and $R_9$, taken together, form a hydrocarbon radical containing 2 to 6 carbon atoms, $R_{10}$ and $R_{11}$ are each independently of the other $C_1$–$C_{12}$alkyl, and $R_{12}$ is hydrogen, $C_1$–$C_8$alkyl, $C_3$–$C_8$cycloalkyl or $C_1$–$C_8$haloalkyl.

In a preferred embodiment of the process, the catalyst is a compound of formula IV or V, wherein $R_6$ and $R_7$ together form a hydrocarbon radical containing 3 to 6 carbon atoms, and $R_8$ and $R_9$ are $C_1$–$C_8$alkyl or $C_5$–$C_6$cycloalkyl, or $R_8$ and $R_9$, taken together, form a hydrocarbon radical containing 2 to 6 carbon atoms, and $R_6$ and $R_7$ are $C_1$–$C_8$alkyl or $C_5$–$C_6$cycloalkyl, or $R_6$ and $R_7$, taken together, form a hydrocarbon radical containing 3 to 6 carbon atoms, and $R_8$ and $R_9$, taken together, form a hydrocarbon radical containing 2 to 6 carbon atoms, $R_{10}$ and $R_{11}$ are each independently of the other $C_1$–$C_4$alkyl and $R_{12}$ is hydrogen, $C_1$–$C_4$alkyl, $C_5$–$C_6$cycloalkyl or $C_1$–$C_4$haloalkyl.

A particularly preferred embodiment of the process comprises using as catalyst an amidine base of formula IV, wherein $R_6$ and $R_7$ together form a saturated hydrocarbon radical of 3 to 6 carbon atoms, and $R_8$ and $R_9$ together form a saturated hydrocarbon radical of 2 to 6 carbon atoms.

Another preferred group of catalysts comprises compounds of formula V, wherein $R_{12}$ is hydrogen or $C_1$–$C_8$alkyl, and $R_{10}$ and $R_{11}$ are identical and are $C_1$–$C_4$alkyl.

Particularly preferred catalysts for the process of this invention are compounds of formula V, wherein $R_{12}$ is hydrogen and the group —$NR_{10}R_{11}$ is in 2 or 4-position, and $R_{10}$ and $R_{11}$ are $C_1$–$C_4$alkyl.

The most preferred catalysts are 1,5-diazabicyclo[4.3.0]non-5-ene, 1,8-diazabicyclo[5.4.0]undec-7-ene, 2-dimethylaminopyridine and 4-dimethylaminopyridine.

The molar ratio of carbonates of formula III to oximes of formula II may typically be from 0.5 to 2.0, preferably from 0.8 to 1.5 and, most preferably, from 0.8 to 1.

Catalytic amounts of an amidine base or pyridine base may typically be from 0.1 to 10 mol %, preferably from 1 to 10 mol % and, most preferably, from 2 to 6 mol %.

The process can be carded out in an organic solvent which is inert to the reactants. It is preferred to use a polar aprotic solvent. A solvents is conveniently used whenever it is desired to isolate the reaction products and to recycle and recover the catalyst and excess starting materials. The optimum conditions can be set by choice of solvent (boiling points). Illustrative examples of suitable organic solvents are aromatic or aliphatic solvents such as benzene, toluene, xylene, mesytilene, hexane, heptane, octane and cyclohexane; aliphatic and aromatic halogenated hydrocarbons such as methylene chloride, chloroform, carbon tetrachloride, trichloroethane, chlorobenzene and dichlorobenzene; ethers such as diethyl ether, dibutyl ether, diisobutyl ether, tetrahydrofuran and dioxane; and also dimethyl sulfoxide and acid amide derivatives such as N,N-dimethylformamide, N,N-dimethylacetamide and N-methyl-2-pyrrolidone; and carboxylates such as ethyl acetate. Preferred solvents are toluene, xylene, dichlorobenzene, chlorobenzene or dimethyl formamide.

The concentration of oxime and carbonate in the reaction mixture when concurrently using a solvent can be from 20 to 60 by volume, preferably from 25 to 50% by volume, based on the solvent.

The process may be carried out in the temperature range from 80° C. to 200° C., preferably from 90° C. to 150° C.

The process may be carried out at atmospheric pressure or slightly above or below atmospheric pressure.

The process may be carried out by slowly adding the oxime or the solution of the oxime to the heated or boiling carbonate or solution of the carbonate. The mixture is then allowed to react for a time, e.g. for 0.5 to 2 hours, and the reaction product is isolated, conveniently by rectification.

Another possibility consists in adding the solution of the carbonate to the oxime prepared in situ from hydroxylamine sulfate and ketone, and isolating the reaction product after a reaction time of e.g. 0.5 to 2 hours.

A further advantage of the inventive process is that the resultant ω-hydroxyalkyloximes do not need to be isolated and can be used as solution in the organic solvent direct for consecutive reactions, so that the synthesis of e.g. herbicides can be substantially simplified.

The invention is illustrated by the following Examples.

EXAMPLE 1

A solution of 160 g (1.81 mol) of ethylene carbonate and 11.02 g (0.07 mol) of 1,8-diazabicyclo[5.4.0]undec-7-ene in 220 g of toluene is heated to reflux in a reactor fitted with reflux condenser, thermometer, dropping funnel and stirrer, and which is provided externally with a temper jacket. A solution of 146.2 g (2.00 mol) of acetone oxime in 217 g of toluene is added dropwise to this solution over a period of 2 hours. Afterwards the reaction solution is kept under reflux for 1 hour until the evolution of $CO_2$ gas has ceased and the conversion of ethylene carbonate is complete. Yield: 722 g of a 24.4 % solution of oxime glycol in toluene, corresponding to a yield of 83.1%. The pure oxime glycol is obtained in a yield of 65 % to 75 %, depending on the desired purity, by carrying out two subsequent rectifications.

EXAMPLE 2

The procedure of Example 1 is repeated, using 13.82 g (0.09 mol) of 1,8-diazabicyclo[5.4.0]undec-7-ene in 220 g of toluene and heating the mixture to reflux. A solution of 146.2 g (2.00 mol) of acetone oxime in 330 g of toluene is added dropwise to this solution over a period of 2 hours. The further steps of Example 1 are carried out, giving 813 g of a 21.4% solution of oxime glycol in toluene, corresponding to a yield of 82.1%. The pure oxime glycol is obtained in a yield of 65% to 75%, depending on the desired purity, by carrying out two subsequent rectifications.

What is claimed is:

1. A process for the hydroxyalkylation of aldoximes and ketoximes by reacting said oximes with unsubstituted or substituted ethylene or propylene carbonate in the presence of a catalyst, which comprises the use of catalytic amounts of a N-alkylated, stable, organic amidine base or a pyridine base which is substituted by a secondary amino group.

2. A process according to claim 1, wherein the amidine base contains the structural element —C—N=C—N—C— and contains a total of 4 to 20 carbon atoms.

3. A process for the preparation of a compound of formula I

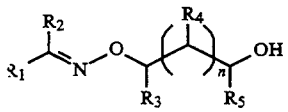
(I)

or wherein $R_1$ and $R_2$ are each independently of the other hydrogen, $C_1$–$C_8$alkyl, $C_3$–$C_8$cycloalkyl, $C_1$–$C_8$haloalkyl, unsubstituted or $C_1$–$C_8$alkyl- or halogen-substituted phenyl, benzyl or phenylethyl, or $R_1$ and $R_2$, taken together, are unsubstituted or $C_1$–$C_8$alkyl- or halogen-substituted $C_2$–$C_7$alkylene, $R_3$, $R_4$ and $R_5$ are each independently of one another hydrogen or $C_1$–$C_8$alkyl, and n is 0 or 1, which comprises reacting a compound of formula II

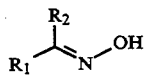
(II)

with a compound of formula III

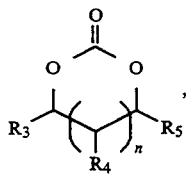
(III)

wherein $R_3$, $R_4$, $R_5$ and n have the meanings given above.

4. A process according to claim 3, wherein $R_1$ and $R_2$ are each independently of the other hydrogen or $C_1$–$C_8$alkyl, or $R_1$ and $R_2$ together form unsubstituted $C_2$–$C_7$alkylene, $R_3$ and $R_5$ are hydrogen or $C_1$–$C_8$alkyl, and n is 0.

5. A process according to claim 3, wherein $R_1$ and $R_2$ are methyl, ethyl or propyl, $R_3$ and $R_4$ are hydrogen, and n is 0.

6. A process according to claim 1, which comprises the use of a catalytic amount of a stable organic amidine base of formula IV or of a pyridine base which is substituted by a secondary amino group, of formula V

(IV)

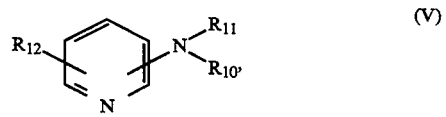
(V)

wherein $R_6$, $R_7$, $R_8$ and $R_9$ are each independently of one another $C_1$–$C_8$alkyl or $C_3$–$C_8$cycloalkyl, or $R_6$ and $R_7$ together form a hydrocarbon radical containing 3 to 6 carbon atoms, and $R_8$ and $R_9$ have the meanings previously given, or $R_8$ and $R_9$, taken together, form a hydrocarbon radical containing 2 to 6 carbon atoms, and $R_6$ and $R_7$ are $C_1$–$C_8$alkyl or $C_3$–$C_8$cycloalkyl, or $R_6$ and $R_7$, taken together, form a hydrocarbon radical containing 3 to 6 carbon atoms, and $R_8$ and $R_9$, taken together, form a hydrocarbon radical containing 2 to 6 carbon atoms, $R_{10}$ and $R_{11}$ are each independently of the other $C_1$–$C_{12}$alkyl, and $R_{12}$ is hydrogen, $C_1$–$C_8$alkyl, $C_3$–$C_8$cycloalkyl or $C_1$–$C_8$haloalkyl.

7. A process according to claim 6, wherein the catalyst is a compound of formula IV or V, wherein $R_6$ and $R_7$ together form a hydrocarbon radical containing 3 to 6 carbon atoms, and $R_8$ and $R_9$ are $C_1$–$C_8$alkyl or $C_5$–$C_6$cycloalkyl, or $R_8$ and $R_9$, taken together, form a hydrocarbon radical containing 2 to 6 carbon atoms, and $R_6$ and $R_7$ are $C_1$–$C_8$alkyl or $C_5$–$C_6$cycloalkyl, or $R_6$ and $R_7$, taken together, form a hydrocarbon radical containing 3 to 6 carbon atoms, and $R_8$ and $R_9$, taken together, form a hydrocarbon radical containing 2 to 6 carbon atoms, $R_{10}$ and $R_{11}$ are each independently of the other $C_1$–$C_4$alkyl and $R_{12}$ is hydrogen, $C_1$–$C_4$alkyl, $C_5$–$C_6$cycloalkyl or $C_1$–$C_4$haloalkyl.

8. A process according to claim 6, wherein the catalyst is an amidine base of formula IV, wherein $R_6$ and $R_7$ together form a saturated hydrocarbon radical of 3 to 6 carbon atoms, and $R_8$ and $R_9$ together form a saturated hydrocarbon radical of 2 to 6 carbon atoms.

9. A process according to claim 6, wherein the catalyst is a compound of formula V, wherein $R_{12}$ is hydrogen or $C_1$–$C_8$alkyl, and $R_{10}$ and $R_{11}$ are identical and are $C_1$–$C_4$alkyl.

10. A process according to claim 6, wherein the catalyst is a compound of formula V, wherein $R_{12}$ is hydrogen and the group —$NR_{10}R_{11}$ is in 2 or 4-position, and $R_{10}$ and $R_{11}$ are $C_1$–$C_4$alkyl.

11. A process according to claim 6, wherein the catalyst is selected from the group consisting of 1,5-diazabicyclo[4.3.0]non-5-ene, 1,8-diazabicyclo[5.4.0]undec-7-ene, 2-dimethylaminopyridine and 4-dimethylaminopyridine.

12. A process according to claim 1, wherein the molar ratio of carbonate of formula III to oxime of formula II is from 0.5 to 2.0.

13. A process according to claim 12, wherein the molar ratio of carbonate of formula III to oxime of formula II is from 0.8 to 1.5.

14. A process according to claim 12, wherein the molar ratio of carbonate of formula III to oxime of formula II is from 0.8 to 1.

15. A process according to claim 1, wherein the catalytic amount of the compound of formula IV or V is from 0.1 to 10 mol %, based on the oxime.

16. A process according to claim 6, wherein the catalytic amount of the compound of formula IV or V is from 1 to 10 mol %, based on the oxime.

17. A process according to claim 6, wherein the catalytic amount of the compound of formula IV or V is from 2 to 6 mol %, based on the oxime.

18. A process according to claim 6, which is carded out in an organic solvent which is inert to the reactants.

19. A process according to claim 18, wherein the concentration of oxime and carbonate, when concurrently using a solvent, is 20 to 60% by volume, based on the solvent.

20. A process according to claim 1, which is carded out in the temperature range from 80° to 200° C.

21. A process according to claim 20, which is carded out in the temperature range from 90° to 150° C.

* * * * *